United States Patent [19]

O'Holleran

[11] Patent Number: 4,744,919

[45] Date of Patent: May 17, 1988

[54] METHOD OF DISPERSING PARTICULATE AEROSOL TRACER

[75] Inventor: Thomas P. O'Holleran, Belleville, Mich.

[73] Assignee: KMS Fusion, Inc., Ann Arbor, Mich.

[21] Appl. No.: 907,112

[22] Filed: Sep. 12, 1986

[51] Int. Cl.$^4$ .............. C09K 3/30; C01N 31/00; C01N 33/00; G01W 1/00

[52] U.S. Cl. .................. 252/305; 73/188; 239/2.1; 252/408.1; 252/965; 502/65; 502/66

[58] Field of Search ............ 252/305, 408.1, 965; 73/188; 239/2.1; 502/65, 66

[56] References Cited

U.S. PATENT DOCUMENTS

| | | | |
|---|---|---|---|
| 2,068,987 | 1/1937 | King, Jr. | 252/305 X |
| 2,232,728 | 2/1941 | Pleasants | 252/305 X |
| 3,072,563 | 1/1963 | Hickson | 252/965 X |
| 3,556,988 | 1/1971 | Stover et al. | 502/65 X |
| 3,751,913 | 8/1973 | Paine et al. | 252/305 X |

*Primary Examiner*—Richard D. Lovering
*Attorney, Agent, or Firm*—Barnes, Kisselle, Raisch, Choate, Whittemore & Hulbert

[57] ABSTRACT

A particulate aerosol tracer which comprises a particulate carrier of sheet silicate composition having a particle size up to one micron, and a cationic dopant chemically absorbed in solid solution in the carrier. The carrier is preferably selected from the group consisting of natural mineral clays such as bentonite, and the dopant is selected from the group consisting of rare earth elements and transition elements. The tracers are dispersed by forming an aqueous salt solution with the dopant present as cations, dispersing the carriers in the solution, and then atomizing the solution under heat sufficient to superheat the solution droplets at a level sufficient to prevent reagglomeration of the carrier particles.

6 Claims, No Drawings

METHOD OF DISPERSING PARTICULATE AEROSOL TRACER

The invention in this application was not made with Government support but was the subject of Government Contract No. DE-AC02-85ER80295 and the Government has certain rights in the invention.

The present invention is directed to atmospheric tracers and to methods of tracer dispersal.

BACKGROUND OF THE INVENTION

Atmospheric pathways for pollutant emission and deposition are under intensive study both in the U.S. and abroad. U.S. Government involvement was established by the Acid Precipitation Act of 1980 and resulted in the establishment of the U.S. Interagency Task Force on Acid Precipitation. The private sector is represented by the Electric Power Research Institute (EPRI). The issues involved are complex, with economic, social and political implications that transcend geopolitical and regional boundaries. In North America, airborne pollution originating from coal-fired electric power plants in the Midwestern U.S. is thought by many to be responsible for damage to the environment and to architectural structures in the Northeastern U.S. and Southeastern Canada. Similar issues have been raised in Western Europe. Regulatory agencies require detailed and accurate information on this phenomenon in order to establish effective guidelines for controlling the problem. The electric power industry needs similar information in order to make sound decisions regarding the economic and engineering aspects of pollution abatement technologies.

Acid rain, as it is called, is primarily an atmospheric phenomenon which implies large-scale and complex behavior. Thus far, the most ambitious attempts to characterize the transport and deposition of these pollutants have used tracer gases released into exhaust plumes, downwind (ground based) detector arrays, and airborne detectors. These studies have produced useful information, but it is known that as much as half of the total sulfate deposited is in the solid state in the form of sub-micron particulates. Gaseous tracers are not well suited for modeling the transport and deposition of solid state pollutants. Particulate tracers, such as oil fog, smoke and die particles, have been used in tracer experiments, but all have drawbacks.

OBJECTS AND SUMMARY OF THE INVENTION

It is therefore a general object of the present invention to provide a solid particulate tracer of sub-micron size, and a method of dispersal, having particular utility in study of atmospheric dynamics, air pollution and the like. A further object of the invention is to provide a tracer and dispersal method of the described character which is economical to implement, and which accommodates simultaneous dynamic study of emission transport and deposition from a number of sources.

Briefly stated, the present invention contemplates a solid sub-micron particulate carrier tagged with a dopant chemically absorbed in solid solution. The dopants are in concentrations not found in background airborne particles, and may thus be distinguished from background employing conventional detection techniques. The particulate carrier in accordance with the invention is an inorganic relatively inert solid in the size range of 0.1 to 1.0 microns, and is compatible with a range of chemical dopants. Bentonite, a naturally occurring clay, satisfies these criteria and is presently preferred. Dopants may comprise rare earth elements such as yttrium and lanthanum, transition elements such as molybdenum, strontium, cobalt, zirconium, gallium and germanium, or mixtures thereof.

The tracers of the invention are dispersed by preparing a slurry of particulate carriers in an aqueous solution of dopant salt, and atomizing the slurry under heat sufficient to decompose the salt. The dopant cation is absorbed into the carrier crystal structure, while the water and anion are evaporated.

DETAILED DESCRIPTION OF PREFERRED EMBODIMENTS

Particulate carriers in accordance with the invention are inorganic biologically inert particles in the sub-micron size range, preferably 0.1 to 1.0 microns. The carrier is chemically compatible with a number of transition and rare-earth dopants—i.e., capable of chemically adsorbing the same. More technically, and in greater detail, the particulate carriers in accordance with the invention are characterized by an ultimate particle size up to one micron when dispersed in water, and a crystal structure which is capable of accommodating or absorbing a wide variety of cations of different sizes and valences. More specifically, in accordance with the invention, carrier particles are of sheet silicate composition.

A presently preferred carrier is bentonite, which is a naturally occurring clay particulate of which more than 95% is less than 1.0 micron in size. Chemically, bentonite is a sodium aluminum hydroxy silicate, with the approximate stoichiometry:

$$(Al, Fe_{1.67}, Mg_{0.33})Si_4O_{10}(OH)_2Na^+Ca_{0.33}^{++}.$$

This material is commercially available and, when dispersed in water, deflocculates to form a suspension in which most of the particles are less than one micron in size. The crystal structure of bentonite accommodates fairly high concentrations of dopant cations with a wide range of ionic sizes and valences. Other suitable carriers are halloysite, hectorite and attapulgite, all of which (including bentonite) are natural mineral clays of sheet silicate composition.

Dopants are selected on the basis of chemical compatibility with the particulate carrier and rarity in natural background air. In demonstration of the invention, strontium, nickel, cobalt and lanthanum were employed. Dopant concentration in the particulate carriers is preferably at least twice that occurring in background aerosol particles in order to obtain unambiguous detection. For urban environments, concentrations of the noted elements have been measured at about 10 to 1000, 1 to 500, 2 to 20 and 1 to 30 nanograms per cubic meter respectively. (Battelle Pac. NW. Lab. Rep. BNWL-SA-4690, June 1, 1973) The valences, ionic radii and ionic field strengths of these elements are representative of a large number of elements in the periodic table. Successful incorporation of these elements as dopants makes over half the known elements potential dopants—i.e., transition elements, the lanthanide series of rare earth elements and the actinide series of rare earth elements.

The doped carriers of the invention are dispersed in the atmosphere as a particulate aerosol. This may be accomplished by dissolving the selected dopant, in the form of a soluble salt, in water. Salt concentration in the range of 10 w/w% to saturation is preferred. The particulate carrier is then added to the solution while constant agitation is maintained. In the case of bentonite, up to 30–40 w/w% carrier can be dispersed in the salt solution without gelation (which is a higher concentration than can be obtained if the carrier is dispersed prior to dissolution of the salt). 25 w/w% is the preferred maximum. The aqueous salt/carrier slurry is then atomized under heat to separate the water, decompose the salt and melt the bentonite, fusing the dopant cation to the bentonite. To prevent bentonite reagglomeration, heating rates must be high enough to superheat the atomized droplets rather than simply evaporate them to dryness. Heating rates, determined primarily by droplet size, in the range of $2.3 \times 10^{6} °C./sec$ to $2.4 \times 10^{6} °C./sec$ are preferred. In demonstration of the invention, a Paasch type H air brush was used as an atomizer, and a Metco oxyacetylene type 6P-II flame spray torch were employed.

It will be appreciated that particulate tracers with differing dopants may be released from a number of differing sources to study atmospheric intermixing and interaction. Thus, emissions or movements from several sources may be studied simultaneously. Any suitable collection and detection technique may be employed, such as X-ray fluorescence or neutron activation analysis.

The invention claimed is:

1. A method of dispersing a particulate aerosol tracer comprising the steps of:
   (a) dissolving in water a soluble salt to form an aqueous salt solution containing cations selected from the group consisting of rare earth elements, transition elements and mixtures thereof,
   (b) dispersing a carrier of sheet silicate composition in said aqueous solution such that said carrier deflocculates to form a dispersion of particles, a major portion of which are less than one micron in size,
   (c) atomizing said solution to form droplets, and
   (d) superheating said droplets to separate the water and chemically fusing the cation into the carrier particles in homogeneously dispersed solid solution throughout the particles.

2. The method set forth in claim 1 wherein said step (d) is carried out by heating said particles at a rate in the range of $2.3 \times 10^{6} °C./sec$ to $2.4 \times 10^{6} °C./sec$.

3. The method set forth in claim 1 wherein said carrier is selected from the group consisting of natural mineral clays.

4. The method set forth in claim 3 wherein said carrier is selected from the group consisting of bentonite, halloysite, hectorite and attapulgite.

5. The method set forth in claim 4 wherein salt concentration in said aqueous solution is in the range of 10 w/w% to saturation, and wherein concentration of said particulate carrier is in the range of up to 30 to 40 w/w%.

6. The method set forth in claim 5 wherein said carrier concentration is about 25 w/w%.

* * * * *